US007967749B2

(12) United States Patent
Hutchinson et al.

(10) Patent No.: US 7,967,749 B2
(45) Date of Patent: Jun. 28, 2011

(54) MONITORING SYSTEM AND METHOD USING RULES

(75) Inventors: George M. Hutchinson, Brookfield, WI (US); Michael O'Reilly, Ann Arbor, MI (US); Kevin K. Tremper, Ann Arbor, MI (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 830 days.

(21) Appl. No.: 10/625,633

(22) Filed: Jul. 23, 2003

(65) Prior Publication Data

US 2005/0020886 A1 Jan. 27, 2005

(51) Int. Cl.
*A61B 5/00* (2006.01)
(52) U.S. Cl. .............................. 600/300; 705/2; 128/920
(58) Field of Classification Search .................. 600/300, 600/301; 128/897, 903–905, 920
See application file for complete search history.

(56) References Cited

U.S. PATENT DOCUMENTS

| | | | | |
|---|---|---|---|---|
| 6,032,678 | A * | 3/2000 | Rottem | 600/437 |
| 6,139,494 | A * | 10/2000 | Cairnes | 600/300 |
| 6,248,063 | B1 * | 6/2001 | Barnhill et al. | 600/300 |
| 6,485,418 | B2 * | 11/2002 | Yasushi et al. | 600/300 |
| 6,497,657 | B2 * | 12/2002 | Nunome | 600/300 |
| 2002/0035315 | A1 * | 3/2002 | Ali et al. | 600/300 |
| 2003/0149526 | A1 * | 8/2003 | Zhou et al. | 701/213 |
| 2004/0122701 | A1 * | 6/2004 | Dahlin et al. | 705/2 |
| 2005/0010088 | A1 * | 1/2005 | Iliff | 600/300 |

* cited by examiner

*Primary Examiner* — Sam Yao
*Assistant Examiner* — Kai Rajan
(74) *Attorney, Agent, or Firm* — Andrus, Sceales, Starke & Sawall, LLP

(57) ABSTRACT

A method of monitoring a subject, such as a patient, using rules is provided. The method includes receiving data from the subject, and applying the data to a rule-based algorithm. The method also preferably includes generating a response based on the application of the rule-based algorithm. Some examples of responses include generating an alarm, generating a suggested reason for an identification of an abnormal condition, and generating a suggested response to an abnormal condition that has been identified. Preferably, more than one set of variables is applied to a particular rule-based algorithm. A monitor using the method may be configured to have multiple rule-based algorithms selected and applied simultaneously. Each rule-based algorithm can generate a unique response, or a combination can be used to generate a smaller number of responses. Also, a monitor using this method may be configured to allow rule-based algorithms to be exchanged and/or altered.

14 Claims, 3 Drawing Sheets

MONITORING SYSTEM AND METHOD USING RULES

TECHNICAL FIELD

The present invention relates generally to a method and apparatus for monitoring, and more particularly, to a method and apparatus for monitoring based on rules and/or sets of rules.

BACKGROUND OF THE INVENTION

Monitoring a subject can be a difficult task that may involve the interpretation of multiple data. Further, many different people may disagree on the proper conclusion based on the data. For instance, one interpretation of the data may suggest that the values are not typical, but are not abnormal either, whereas a second interpretation may suggest that an abnormal condition does exist. Further, one group may feel that a particular situation may be identified based on one set of data, whereas another group might identify the same situation using different data, or giving different weight to the different portions of the data. A monitoring system that would allow multiple interpretations to be made would be preferable. A monitoring system that displays each of the multiple interpretations to a user would be more preferable.

Also, a group of people writing one set of rules may be known as experts in one field, but may not be as experienced in another. Further, different groups may have different philosophies for treating patients, thus, given the same data, different groups may suggest different treatment options. Also, one group's interpretation may be better suited to subjects with one set of characteristics, while another group's interpretation is better suited to a subject with a different set of characteristics (for instance children v. the elderly, etc). A monitoring system that allows different interpretations to be used in different situations would be preferable.

Additionally, proper identification of an abnormal condition can sometimes involve the values of one set of data in comparison to values of another set of data. These data must often be obtained from different sensors which may be monitoring the same characteristic using a different technique, or which may be monitoring a different, but related, characteristic. Any single interpretation of the data would preferably be able to use data acquired from multiple sensors such that some of the more complex relationships may be identified.

While most clinicians possess sufficient training and experience to adequately interpret a plurality of variables, it places considerable effort and time constraints on the medical staff. Additionally, interpretation of the complex plurality of variables is often difficult. Further, some conditions are extremely rare and may not be known to every clinician, especially if the extremely rare condition is outside of their specialty. While a clinician can look up the condition and understand it on his own, emergency situations tend not to afford a clinician that opportunity. A system that could aid a clinician's interpretation of monitoring data would be preferable.

The teachings hereinbelow extend to those embodiments which fall within the scope of the appended claims, regardless of whether they accomplish one or more of the above-mentioned needs.

SUMMARY OF THE INVENTION

A method and apparatus for patient physiologic monitoring is provided. The method includes receiving a real-time physiologic data stream from a patient. The real-time physiologic data stream includes a plurality of physiologic variables. The method further includes processing the plurality of physiologic variables using a rules engine. At least one interpretation of the plurality of physiologic variables is generated utilizing the rules engine.

Another embodiment is directed to a method for monitoring a patient. The method comprises acquiring data from the patient based on continuous monitoring, applying a rule-based algorithm based on the data, and generating a response based on the application of the algorithm.

Another embodiment provides a method for monitoring a subject. The method comprises storing a plurality of rule-based algorithms that can generate different responses, determining which rule-based algorithm to apply, acquiring data relating to the subject from a sensor, applying at least one of the plurality of rule-based algorithms based on the data, and generating a response based on the application of at least one of the plurality of rule-based algorithms.

An additional embodiment provides a method for generating a response relating to a subject. The method comprises acquiring data relating to the subject, applying a plurality of rule-based algorithms, and generating a plurality of interpretations of the data based on the application of the plurality of algorithms.

Another embodiment is directed to a method for monitoring a subject. The method comprises acquiring data from more than one sensor coupled to the subject, applying the data to a rule-based algorithm, and generating a response based on the application of the data to the rule-based algorithm.

Another embodiment provides a monitoring system using rule-based algorithms. The system comprises a data storage device configured to store rule-based algorithms, and a network interface configured to transfer rule-based algorithms across a network to the data storage device.

An additional embodiment is directed to a method for monitoring a patient. The method comprises acquiring data from a monitor that is monitoring a patient, and suggesting a reason for an abnormal condition that is identified when the data is applied to a rule-based algorithm.

Other features of the present invention will become apparent when viewed in light of the detailed description of the preferred embodiment when taken in conjunction with the attached drawings and appended claims.

DETAILED DESCRIPTION OF THE PREFERRED EMBODIMENTS

Figure 1:
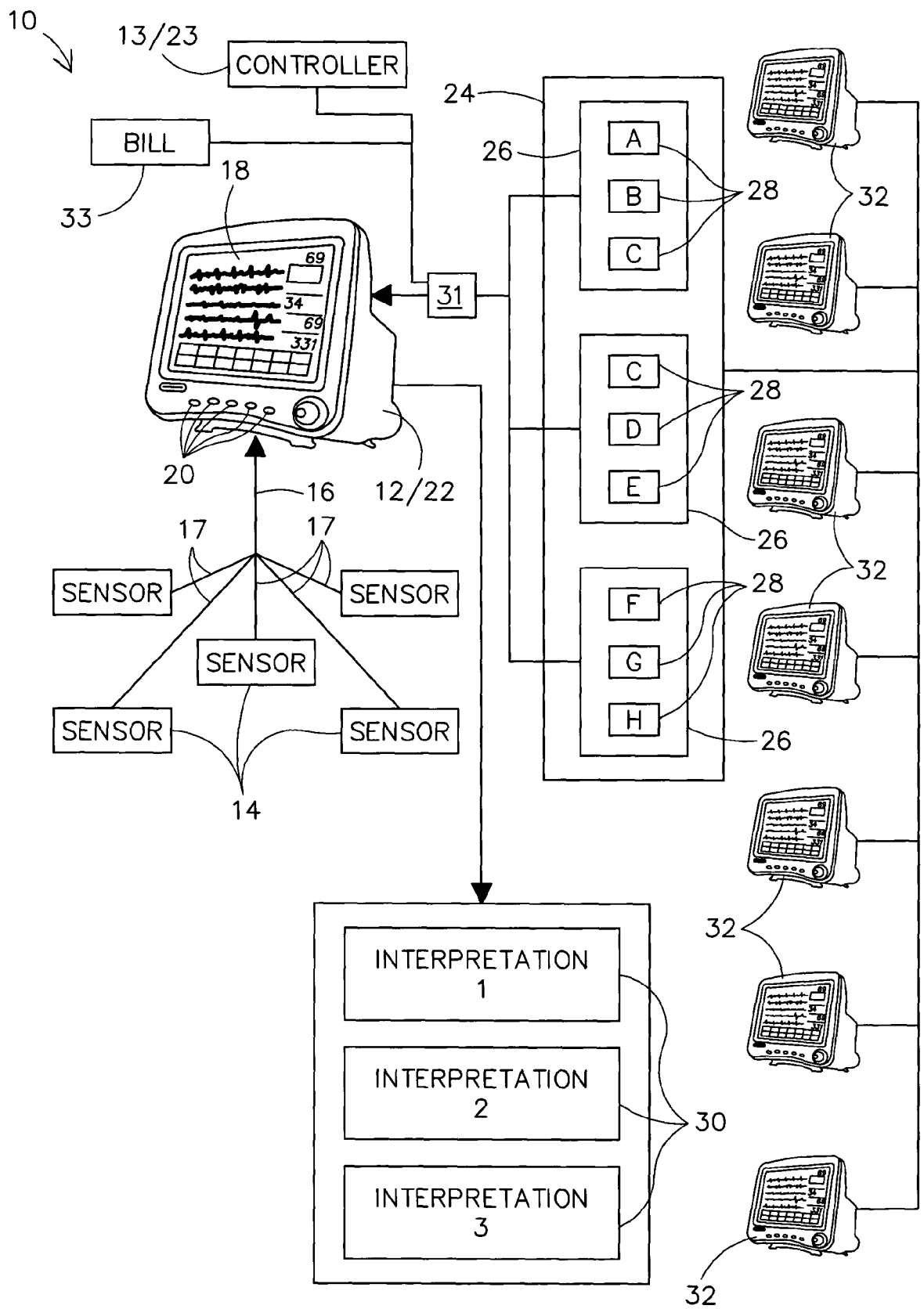
FIG. 1 is an illustration of a physiologic monitoring system in accordance with one exemplary embodiment of the present invention.

Referring now to FIG. 1, which is an illustration of a patient physiologic monitoring assembly 10 in accordance with the present invention. The patient physiologic monitoring assembly 10 includes a controller 12 in communication with a plurality of patient sensors 14 in order to receive a real-time physiologic data stream 16. It is contemplated that the patient sensors 14 and real-time physiologic data stream 16 may encompass a wide variety of patient monitoring physiologic characteristics/variables 17. These variables include, but are not limited to, heart rate, arterial blood pressure, $SpO_2$, $CO_2$, respiration rate, and a variety of other patient physiologic responses. It should be understood that a wide variety of such responses and sensors 14 designed to receive them are contemplated by the present invention. Similarly, a host of amplifiers, filters, and digitization elements may be utilized in combination with the sensors 14 as would be understood by one skilled in the art. The controller 12 may be utilized in combination with a variety of interactive elements such as a display 18 and user interface 20 as would be comprehended by one skilled in the art. User interface 20 can be used to facilitate the transfer of rule-based algorithms to and from the system. For instance, user interface 20 may aid a user in obtaining a rule-based algorithm from within a health care facility's network (i.e. networks are often established within a doctor's office, a hospital, a hospital campus, a group of co-managed or affiliated facilities), or from a source outside the health care facility's network. Preferably, the transferred rule-based algorithms (rule 28 or rule set 26) can be written by different groups and be used interchangeably and/or in combination.

Figure 2:
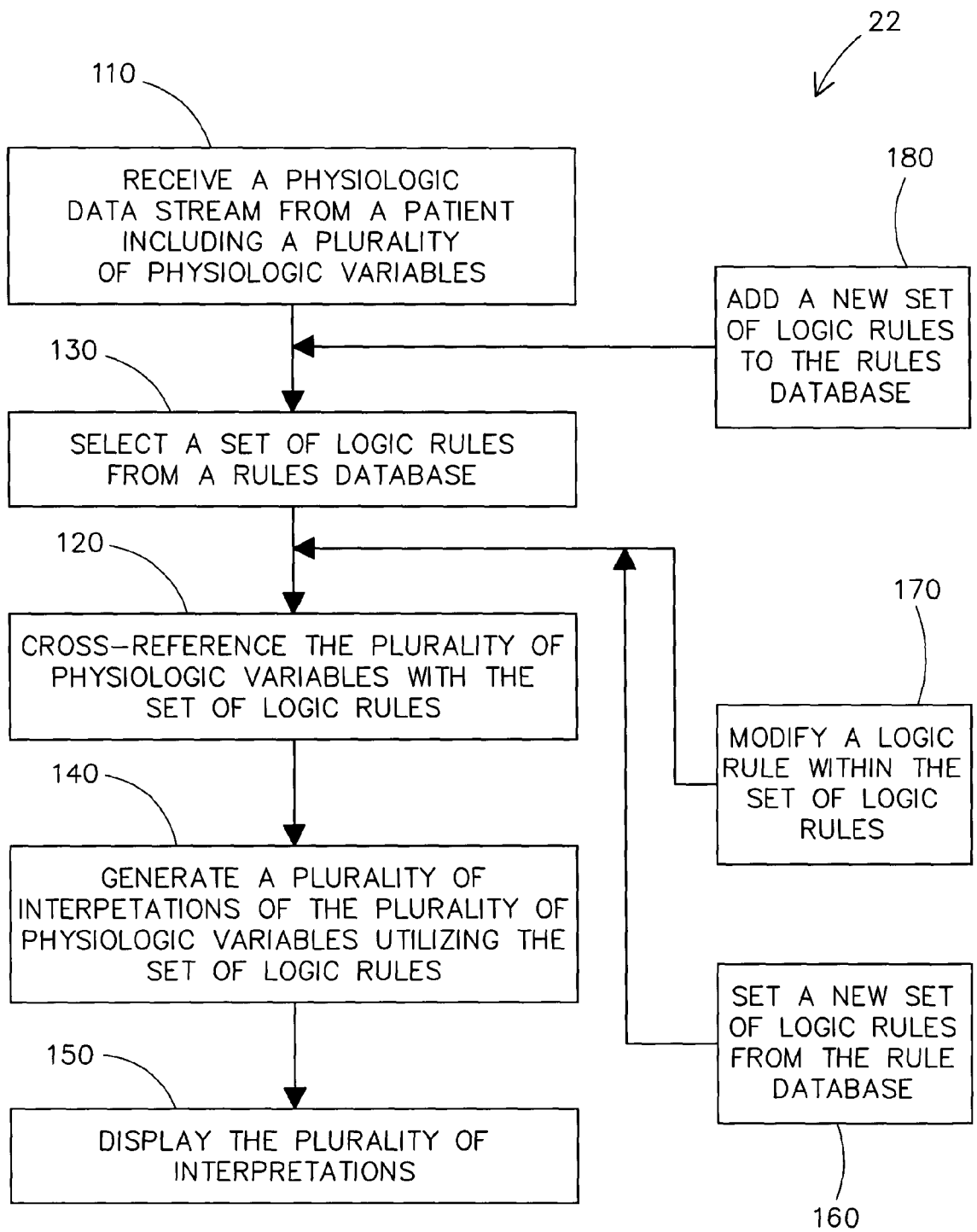
FIG. 2 is a flow-chart illustration of a physiologic monitoring system in accordance with another exemplary embodiment of the present invention.

The controller 12 includes a logic 22 adapted to perform a plurality of functions as is illustrated in FIG. 2. It should be understood that although the terms controller 12 and logic 22 are utilized in the singular vernacular, a plurality of individualized controllers 12 and logic elements 22 could be used in combination to practice the present invention and are contemplated as incorporated into the chosen vernacular. The logic 22 is adapted to receive a physiologic data stream including a plurality of physiologic variables 110 of the patient. The logic 22 is further adapted to cross-reference the plurality of physiologic variables with a set of logic rules 120. The preferred embodiment contemplates the use of a data storage device 24 such as a rules database comprised of a plurality of logic rules 28 and rule sets 26. Within each logic rule set 26 is a plurality of logic rules 28. These logic rules 28 are comprised of diagnostic algorithms that allow the plurality of physiologic variables 17 to be correlated with a diagnostic interpretation 30. By way of example, one physiologic variable 17 may indicate a drop in oxygen in a patient's blood. Another physiologic variable 17 may indicate the level of $CO_2$ that a patient exhales is dropping as well. A logic rule 28 can be adapted such that these physiologic variables 17 in combination correlate with a diagnostic interpretation 30 indicating a reduction in a patient's circulation. Although a single example has been provided, it should be understood that a wide variety of such logic rules 17 are possible. Logic rule-based algorithms can be pre-assigned to particular sets, or sets can be modified by an individual user. For instance, a hospital or an individual clinician might have a preferred grouping of rules which can be applied as a set. Further, sets of rule-based algorithms may be classified based on an area of interest, such as a rule set which contains a plurality of rules designed to monitor the cardiovascular system. Further still, a set may include all of the rules in a particular database. Rules may be uniquely assigned to a particular set, there may be overlap of rules in some rule sets, a set may be controlled by a file which accesses the individual rules from a mass database of rules, a combination of these systems may be used, or some other system may be used. If there is overlap between sets, and multiple sets may be applied at a time, the logic may be adapted to identify redundant rules and to prevent the redundant rule from being applied.

A potential advantage of this exemplary embodiment stems from the fact that the present embodiment stores a plurality of logic rules 28 within each of the logic rule sets 26. This allows a plurality of diagnostic interpretations 30 to be provided to a clinician from the physiologic data stream 16. Thus, a clinician can be provided with alternate and differing interpretations that allow him to utilize his personal medical knowledge to choose the preferred interpretation, perform follow up examinations to deduce the preferred interpretation, and/or recognize the existence of more than one condition that may be manifesting itself within the patient.

It is contemplated that the logic rule sets 26 may be organized in a variety of fashions such that a category of diagnostic logic rule-based algorithms 28 may be selected. It is contemplated that the logic 22 may be adapted to select a set of logic rules from the rules database 130 (the logic is designed such that one or more rule-based algorithms may be applied at a time). This may be accomplished in a variety of fashions. One embodiment contemplates allowing the clinician to select the logic rule set 26 in accordance with the type of diagnostic monitoring desired for a given patient. Another embodiment, however, contemplates the logic 22 utilizing the physiologic data stream 16 and the physiologic variables 17 to select a logic rule set 26 or group of logic rule sets 26 in accordance with the physiologic variables 17 it finds itself receiving. Thus, only the logic rules sets 26 capable of, or best suited to, interpreting the available physiologic variables 17 could be selected; the logic rule sets to be applied would be based on the analysis of the data currently being made by one or more algorithms.

The logic 22 is then adapted to generate a plurality of diagnostic interpretations of the plurality of physiologic variables utilizing the set of logic rules 140. Again, this generation of diagnostic interpretations 140 can be based on a single set of rules 26 or a grouping of sets. The logic 22 further displays the plurality of diagnostic interpretations 150. It is contemplated that the display may take on a variety of embodiments. One embodiment contemplates a display on the display element 18. Other embodiments contemplate a printed display or an entry into a patient's medical file.

Another potential advantage of the present exemplary embodiment is that the logic 22 is adapted to allow a user to select a new set of logic rules from the rule database 160. Therefore, a clinician can utilize the monitor to generate a first plurality of diagnostic interpretations 150. The clinician can additionally select a new set of logic rules 160 and thereby generate a second plurality of diagnostic interpretations 150. This feature may be used for a variety of applications. This feature may be utilized as an effective second opinion as compared to the first set of interpretations. Alternatively, follow up or additional concerns may arise from the first set of interpretations that may induce a clinician to require interpretations contained in an additional set of logic rules 26. By way of example, the aforementioned interpretation that predicted a decrease in circulation may give rise to a clinician to select a set of logic rules 26 that dealt specifically with cardiovascular interpretations. Thus, the second set of interpretations might provide a plurality of interpretations directly applicable to a patient's heart condition. In this fashion, a physician may be provided with a number of diagnostic interpretations 30, without subjecting the clinician to interpretations being made by algorithms that are not as relevant to the problem(s) with which the clinician is concerned.

The present exemplary embodiment also incorporates flexibility in regards to the rules database 24 that increases both its accuracy and usefulness. The present exemplary embodiment includes the ability to modify a logic rule within a logic rules set 170. The term modify is intended to incorporate the ability to add, edit, or delete a logic rule 28 within a logic rules set 26. This allows a clinician utilizing the present exemplary embodiment to advance the technology of the monitoring system 10 through the addition of his own expertise. If a clinician determines a diagnostic statement 30 arising from a logic rule 28 to be inaccurate or incorrect, the clinician can either delete the logic rule 28 in question or edit it such that it produces the diagnostic statement 30 in a manner that is more desirable. Similarly, if the clinician recognizes that a grouping of physiologic variables 17 should result in a particular diagnostic statement 30, the clinician has the ability to add that logic rule 28 to the rules database 24.

It is contemplated that although individual clinicians utilizing the monitoring system 10 may effectuate changes on the rules database 24, it is also desirable for the logic rules 28 to be developed by experts within specialized fields of medicine. Thus, the present exemplary embodiment adapts the logic to add a new set of logic rules to the rules database 180. These new sets may replace existing rule sets 26 or may be added in addition to existing rule sets 26. In this fashion, specialized research facilities or renowned experts in specific medical fields may develop rule sets 26 that local medical facilities may add to their own rules database 24. That way, the rule-based algorithms can be drawn from varying groups who are unrelated (i.e. they come from different companies, research institutions, and/or health care facilities which are not affiliated for the purpose of creating the rule-based algorithms). This can significantly improve the resources available to small entity physicians as well as interns and new physicians. The plurality of diagnostic statements 30 generated can allow a clinician with little or no expertise in a field to accurately diagnose conditions he may have otherwise required an expert to recognize. It is contemplated that these new sets of logic rules 26 may be made a available in a variety of fashions. For instance, rule sets may be available as a downloadable, or otherwise accessible, file from the internet, may be available on a computer readable medium, may be transferred wirelessly to the monitor, may be transferable across a health care facility's network (a network primarily established to connect the properties, equipment, and equipment of a health care facility—typically established as an intranet, WAN, or LAN), some combination of these methods, etc.

One embodiment contemplates the sale of logic rule sets 26 as packages developed by individual expert consortiums or groups. Another embodiment contemplates their availability through a network 32 of monitors or medical facilities such that expertise in diagnosis can be pooled over the network 32 of facilities. This will allow an improvement in speed an accuracy of patient diagnosis over a large group of caregivers.

If a network 32 of facilities is used, each facility and/or monitoring system could include a network interface 31 that facilitates access to the network. A controller 13 would include logic 23 configured to control the transfer of rules-based algorithms across network 32. Algorithms could be transferable from a monitoring system to a data storage device (such as storing an algorithm that has been tailored to an individual and/or otherwise modified), they could be transferable within a health care facility, and/or they can be transferred amongst a number of facilities. Controller 13 could be configured to limit access to the rule-based algorithms. For instance, only people meeting a certain predetermined criteria may have access to the rule-based algorithms, or certain sets of the rule-based algorithms. The predetermined criteria may be the payment of a fee, being a member of a group or sub-group, being a user who has registered, being a user who has contributed to the development of the rule-based algorithms, etc. When algorithms are transferred a record of the transfer can be made. These records can be used for many purposes. For instance, a bill generator 33 may be used to generate a bill based on transference of the algorithms.

Figure 3:
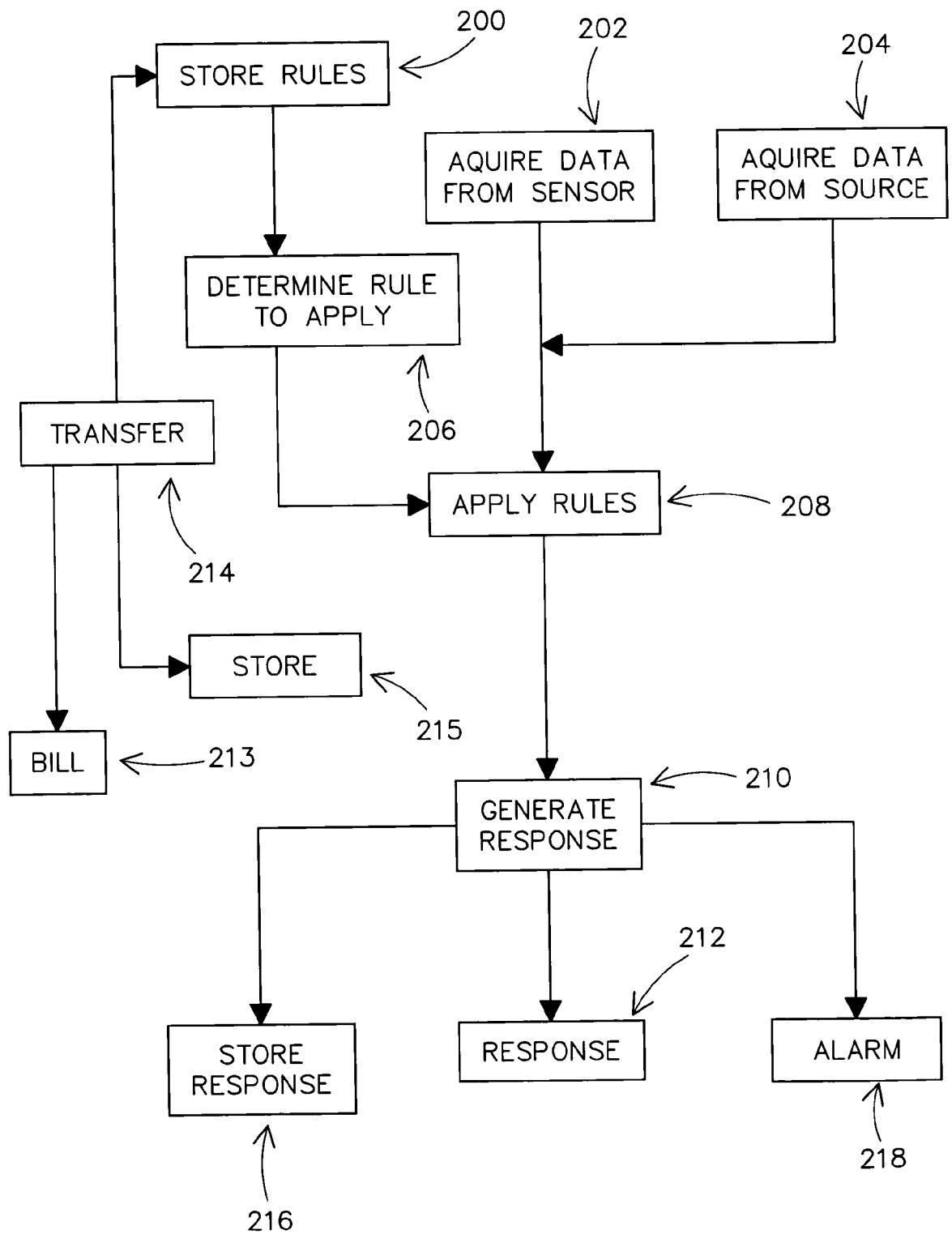
FIG. 3 is a flow-chart illustration of a subject monitoring system in accordance with another exemplary embodiment of the present invention.

Referring to FIG. 3, a method for monitoring includes storing a set of rule-based algorithms at block 200 (stored within a monitoring system's memory or within a health care facility's network) and block 215 (stored remote from the monitoring system and/or heath care facility's network). Each of the rule-based algorithms can be capable of generating a different response when applied to the same data. The rules to be applied are then determined at block 206. Determining which rules to apply can vary based on a number of factors. A rule or set of rules can be chosen by a user (such as from a list generated for the user), can be chosen based on characteristics of a subject, can be chosen based on the reason the subject is being monitored, and/or some other factor or combination of factors. The rules preferably relate, at least in part, to vital signs/physiologic characteristics of a health care patient. The rules can be used to identify an occurrence of an event, such as a pattern, a sequence, and/or a combination of data. The rules are preferably able to be used to generate diagnostic interpretations, or at least information related to a diagnostic interpretation.

Data is acquired at block 202. The data can be acquired from a single sensor, or a plurality of sensors, that are coupled to a subject (preferably a medical patient). If more than one sensor is being used, the sensors can be used to monitor a single characteristic of the subject being monitored (such as by using a variety of different techniques), a variety of characteristics of the subject being monitored, or some combination thereof. Data can be acquired from sources other than a sensor at block 204. The data at block 204 can come from a user input, a file relating to the subject, a database of information (which may include a file relating to the subject), or some other non-subject source.

The selected rule-based algorithm(s) are then applied based on the data at block 208. The rule-based algorithm(s) are used to generate a response at block 210. The response can be an alarm 218, an indication of an abnormal event, a list of problems, a diagnostic interpretation (or related information), a suggestion, or some other response. Information related to a diagnostic interpretation could include an interpretation of the data, a citation of resources which would aid a clinician in making a diagnosis, suggested tests or actions to take to make a diagnosis, a list of potential interpretations, a suggested response to an abnormal condition that may exist, and other similar information. Further, the response can include a plurality of views if a plurality of rule-based algorithms are used. For instance, one rule-based algorithm may give one suggestion and another rule-based algorithm would give another. If more than one view is generated, the views may be combined to give a certainty score (i.e. if five rule-based algorithms are used and they all agree, there is a stronger degree of certainty, whereas if only three agree then certainty is less clear). Also, the views may be combined to generate an alarm 218, or a series of alarms depending on the amount of agreement between the rule sets. Even more, a single value for a characteristic can be generated based on the various data applied to a rule-based algorithm and/or based on the combination of the results of various rule-based algorithms.

The response or responses can then be displayed at block 212. The responses can also be stored at block 216, such as in a record relating to the subject or the monitoring. The stored response can be used to later evaluate the effectiveness of the rule-based algorithms, and/or be used to later supply data relating to the subject.

Rule-based algorithms can also be transferred to and from the set of stored rules at block 214. For instance, the rules database from which the rules to be applied are drawn may only temporarily store the rules for the purpose of applying the rules to the data. Also, rules can be added to (increase the number of stored rules) or removed from (decrease the number of stored rules) the rules database drawn from by a monitoring system. Transfer of the rule-based algorithms can be accomplished with any number of data transfer devices. For instance, an electronically recordable medium or a network interface may be used. Transfer of rule-based algorithms from one facility to another facility, as mentioned earlier, can be limited by any number of predetermined criteria. Further a bill can be generated at block 213 based on the transfer of data at block 214.

The invention has been described with reference to various specific and illustrative embodiments and techniques. However, it should be understood that many variations and modifications may be made while remaining within the spirit and scope of the invention. For instance, while the invention is particularly useful for patient monitoring, some aspects of the invention are applicable to other monitoring activities. Also, reference to multiple controllers is not meant to mean that the controllers are physically separate and distinct. Additionally, reference to a list of rule-based algorithms to apply could encompass a system that only applies one rule-based algorithm at a time.

What is claimed is:

1. A patient physiologic monitoring assembly comprising:
a plurality of sensors that generate a real-time physiologic data stream, said real-time physiologic data stream including a plurality of physiologic variables;
a first logic rule set for diagnosing a physiological condition of a patient, the first logic rule set including a plurality of logic rules for interpreting the plurality of physiologic variables of the real-time physiologic data stream;
a second logic rule set for diagnosing the physiological condition of the patient, the second logic rule set including a plurality of logic rules for interpreting the physiologic variables of the real-time physiologic data stream; and
a controller that receives said real-time physiologic data stream as the data stream is generated, said controller including a logic that:
simultaneously cross references said plurality of physiologic variables of the real-time physiologic data stream with the first logic rule set and second logic rule set as the controller receives the real-time physiologic data system;
generates at least a first diagnostic interpretation of said plurality of physiologic variables utilizing said first logic rule set and a second diagnostic interpretation of said plurality of physiologic variables utilizing said second logic rule set; and
displays said first and second diagnostic interpretations on a display element;
wherein the first diagnostic interpretation and the second diagnostic interpretations are different diagnostic interpretations of the same physiological condition, using the same real-time physiologic data stream.

2. A patient physiologic monitoring assembly as described in claim 1, wherein said logic is further adapted to select said first logic rule set and said second logic rule set from a rules database, said rules database including a plurality of logic rule sets.

3. A patient physiologic monitoring assembly as described in claim 2, wherein said logic is further adapted to modify one of said plurality of logic rules within said first logic rule set.

4. A patient physiologic monitoring assembly as described in claim 3, wherein said logic edits one of said plurality of logic rules.

5. A patient physiologic monitoring assembly as described in claim 3, wherein said logic deletes one of said plurality of logic rules.

6. A patient physiologic monitoring assembly as described in claim 3, wherein said logic adds a new logic rule to said first logic rule set.

7. A patient physiologic monitoring assembly as described in claim 2, wherein said logic is further adapted to add a new logic rule set to said rules database.

8. A patient physiologic monitoring assembly as described in claim 1, further comprising a plurality of networked medical facilities in communication with said controller such that said first logic rule set may be received from any of said plurality of networked medical facilities.

9. A method for providing diagnostic aid to a clinician monitoring the medical condition of a patient, the method comprising:
storing a plurality of sets of rule-based algorithms, including a first and a second set of rule-based algorithms on a data storage device, the first and second sets of rule-based algorithms generating different diagnostic interpretations of the same physiological data representative of the same physiological system;
acquiring a physiological data stream from at least one sensor connected to the patient;
identifying, with a logic of a controller, physiological data present in the physiological data stream;
selecting, with the logic of the controller, the first and second sets of rule-based algorithms that generate different diagnostic interpretations of the identified physiological data in the physiological data stream;
applying with the logic of the controller, at least one rule-based algorithm from the first set of the rule-based algorithms to the physiological data stream as the physiological data stream is acquired;
generating a first diagnostic interpretation with the controller based on the application of the at least one rule-based algorithm from the first set to the acquired physiological data stream;
displaying the first diagnostic interpretation to the clinician;
applying with the logic at least one rule-based algorithm from the second set of rule-based algorithms to the acquired physiological data stream as the physiological data stream is acquired;
generating with the controller a second diagnostic interpretation based on the application of the at least one rule-based algorithm from the second set to the acquired physiological data stream; and
displaying the second diagnostic interpretation to the clinician.

10. A method for diagnosing the medical condition of a patient, the method comprising:
acquiring at least one real-time physiological data stream;
identifying, with a logic operating on a controller, a physiological data present in the at least one real-time physiological data stream;
selecting, with the logic, a first rule set comprising rule-based algorithms directed to produce at least one first diagnostic interpretation of the physiological data;
selecting, with the logic, a second rule set comprising rule-based algorithms directed to produce at least one second diagnostic interpretation of the physiological data, wherein the first rule set and the second rule sets produce different diagnostic interpretations of the same identified physiological data;

applying, with the logic the first rule set to the at least one real-time physiological data stream as the at least one real-time physiological data stream is acquired to produce at least one first diagnostic interpretation;

applying, with the logic, the second rule set to the at least one real-time physiological data stream as the at least one real-time physiological data stream is acquired to produce at least one second diagnostic interpretation; and displaying at the first and second diagnostic interpretations.

11. The method of claim 10, further comprising generating a certainty score for each of the first and second diagnostic interpretations, wherein the certainty score provides comparative information about the first and second diagnostic interpretations.

12. The method of claim 10 wherein the physiological data identified in the at least one real-time physiological data stream identifies the cardiac system and the at least one first and second diagnostic interpretations are differing diagnosis of cardiological conditions.

13. The method of claim 10, wherein the at least one real-time physiological data stream is a plurality of real-time physiological data streams wherein each of the plurality of real-time physiological data streams monitor the same physiological system using different monitoring techniques.

14. The method of claim 10, wherein the at least one real-time physiological data stream is a plurality of real-time physiological data streams wherein each of the plurality of real-time physiological data streams are from separate physiological systems of the patient.

* * * * *

UNITED STATES PATENT AND TRADEMARK OFFICE
CERTIFICATE OF CORRECTION

| | | |
|---|---|---|
| PATENT NO. | : 7,967,749 B2 | Page 1 of 1 |
| APPLICATION NO. | : 10/625633 | |
| DATED | : June 28, 2011 | |
| INVENTOR(S) | : Hutchinson et al. | |

It is certified that error appears in the above-identified patent and that said Letters Patent is hereby corrected as shown below:

On the Face Page, in the Figure, for Tag "140", in Line 2, delete "INTERPETATIONS" and insert -- INTERPRETATIONS --, therefor.

In Fig. 2, Sheet 2 of 3, for Tag "140", in Line 2, delete "INTERPETATIONS" and insert -- INTERPRETATIONS --, therefor.

In Column 5, Line 32, delete "a available" and insert -- available --, therefor.

In Column 5, Line 47, delete "speed an" and insert -- speed and --, therefor.

In Column 8, Line 35, in Claim 9, delete "applying" and insert -- applying, --, therefor.

In Column 9, Line 3, in Claim 10, delete "logic" and insert -- logic, --, therefor.

In Column 9, Line 12, in Claim 10, after "displaying" delete "at".

Signed and Sealed this
Twenty-fifth Day of October, 2011

David J. Kappos
*Director of the United States Patent and Trademark Office*